United States Patent
Anderson et al.

(10) Patent No.: US 8,026,230 B2
(45) Date of Patent: Sep. 27, 2011

(54) METHODS AND COMPOSITIONS FOR TREATING CANCER USING PROTEASOME INHIBITORS

(75) Inventors: Kenneth C. Anderson, Wellesley, MA (US); Teru Hideshima, Brookline, MA (US); Constantine S. Mitsiades, Boston, MA (US); Nicholas Mitsiades, Framingham, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 553 days.

(21) Appl. No.: 11/119,473

(22) Filed: Apr. 29, 2005

(65) Prior Publication Data

US 2005/0267037 A1     Dec. 1, 2005

Related U.S. Application Data

(63) Continuation of application No. PCT/US03/035513, filed on Nov. 6, 2003.

(60) Provisional application No. 60/424,363, filed on Nov. 6, 2002.

(51) Int. Cl.
*A61K 38/08* (2006.01)
*A61K 38/05* (2006.01)
*A61K 31/04* (2006.01)

(52) U.S. Cl. .............. 514/183; 514/34; 514/16; 514/18

(58) Field of Classification Search ................. 514/183, 514/34, 16, 18
See application file for complete search history.

(56) References Cited

U.S. PATENT DOCUMENTS

| | | | |
|---|---|---|---|
| 5,693,617 | A | 12/1997 | Stein et al. |
| 5,919,815 | A | 7/1999 | Bradley et al. |
| 2002/0041874 | A1 | 4/2002 | Mundy et al. |
| 2002/0049157 | A1* | 4/2002 | Wu et al. ............... 514/9 |
| 2002/0068690 | A1 | 6/2002 | Baldwin et al. |
| 2002/0107203 | A1 | 8/2002 | Mundy et al. |

FOREIGN PATENT DOCUMENTS

| | | |
|---|---|---|
| EP | 0 393 457 | 7/1994 |
| EP | 0 363 284 | 5/1997 |
| EP | 0 364 344 | 5/1998 |
| EP | 1 153 612 | 11/2001 |
| JP | 2007-224053 | 9/2007 |
| WO | WO 88/10266 | 12/1988 |
| WO | WO 91/13904 | 9/1991 |
| WO | WO 92/01850 | 2/1992 |
| WO | WO 92/12140 | 7/1992 |
| WO | WO-95/25533 | 9/1995 |
| WO | WO-99/22729 | 5/1999 |
| WO | WO 01/13904 | 3/2001 |

OTHER PUBLICATIONS

Ma et. al., CAS accession No. 2002:241246, corresponding to Blood (Nov. 16, 2001) 98 (11): part 1, pp. 473a (43rd annual meeting of the American Society of Hematology, Part 1, Orlando, Florida, USA).*
Hideshima et. al., Cancer Research (Apr. 1, 2001) 61:3071-3076.*
Gura et. al. (Science, 1997, 278:1041-1042).*
Johnson et. al. (British Journal of Cancer, 2001, 84:1424-1431).*
Hideshima et. al. (Cancer Research (2001) 61:3071-3076).*
Goodman and Gilman's The Pharmacological Basis of Therapeutics (Tenth Edition (2001), McGraw Hill, Chapter I, pp. 3-29).*
Angelastro et al., "Alpha-diketone and alpha-keto ester derivatives of N-protected amino acids and peptides as novel inhibitors of cysteine and serine proteinases," J. Med. Chem. 33:11-3 (1990).
Angliker et al., "The synthesis of lysylfluoromethanes and their properties as inhibitors of trypsin, plasmin and cathepsin B," Biochem. J. 241:871-875 (1987).
Bossy-Wetzel et al., "Assays for cytochrome c release from mitochondria during apoptosis," Methods in Enzymol. 322:235-42 (2000).
Bossy-Wetzel et al., "Detection of apopotosis by by annexin V labeling," Methods in Enzymol. 322:15-18 (2000).
Darzynkiewicz et al., "Analysis of apoptotic cells by flow and laser scanning cytometry," Methods in Enzymol., 322:18-39 (2000).
Dick et al., "Degradation of Oxidized Insulin B Chain by the Multiproteinase Complex Macropain (Proteasome)," Biochem. 30:2725-2734 (1991).
Ewoldt et al., "Sulfonyl fluoride serine protease inhibitors inactivate RNK-16 lymphocyte granule proteases and reduce lysis by granule extracts and perforin," Mol. Immunol. 29(6):713-721 (1992).
Featherstone et al., "DNA double-strand break repair," Curr Biol 9:R759-R761 (1999).
Goldberg et al., "Proteolysis, proteasomes and antigen presentation," Nature 357:375-379 (1992).
Goldberg, "The mechanism and functions of ATP-dependent proteases in bacterial and animal cells," Eur. J. Biochem. 203:9-23 (1992).
Green et al., "Peptidyl Diazomethyl Ketones are Specific Inactivators of Thiol Proteinases," J. Biol. Chem. 256:1923-1928 (1981).

(Continued)

*Primary Examiner* — Marcos L Sznaidman
(74) *Attorney, Agent, or Firm* — Foley Hoag, LLP (57) ABSTRACT

The present invention relates to therapeutic compositions for treating cancer or preventing the growth of cancer cells, e.g., tumor growth, in a subject. The present invention also relates to methods for treating cancer, e.g., inhibiting tumor growth, in a subject who has become resistant to treatment, by administering to a subject an effective amount of a proteasome inhibitor and an effective amount of a therapeutic agent, e.g., a chemotherapeutic agent. The present invention further relates to methods for purging bone marrow, i.e., removing cancer cells from bone marrow, by exposing the bone marrow cells to a proteasome inhibitor and a therapeutic agent, e.g., a chemotherapeutic agent.

18 Claims, 6 Drawing Sheets

OTHER PUBLICATIONS

Hanada et al., "Characterization of the three new analogs of E-64 and their therapeutic application," Proteinase Inhibitors: Medical and Biological Aspects, Katunuma et al., Eds. Springer-Verlag pp. 25-36 (1983).

Hernandez et al., "Effect of the 7-amino substituent on the inhibitory potency of mechanism-based isocoumarin inhibitors for porcine pancreatic and human neutrophil elastases: a 1.85-A X-ray structure of the complex between porcine pancreatic elastase and 7-[N-tosylphenylalanyl)amino]-4-chloro-3-methoxyisocoumarin," J. Med. Chem. 35(6):1121-1129 (1992).

Hudig et al., "The function of lymphocyte proteases. Inhibition and restoration of granule-mediated lysis with isocoumarin serine protease inhibitors," J. Immunol. 147(4):1360-1368 (1991).

Hudig et al., "Selective isocoumarin serine protease inhibitors block RNK-16 lymphocyte granule-mediated cytolysis," Mol. Immunol. 26(8):793-798 (1989).

Hughes, F.M., "Apoptotic Nuclease Assays," Methods in Enzymol., 322:47-62 (2000).

Kajiwara et al., "Elucidation of calpain dependent phosphorylation of myosin light chain in human platelets," Biochem. Int. 15:935-944 (1987).

Kam et al., "Mechanism-Based Isocoumarin Inhibitors for Trypsin and Blood Coagulation Serine Proteases: New Anticoagulants," Biochem. 27(7):2547-2557 (1988).

Kam et al., "Thioester Chromogenic Substrates for Human Factor Vlla: Substituted Isocoumarins are Inhibitors of Factor Vlla and In Vitro Anticoagulants," Thrombosis and Haemostasis 64(1):133-137 (1990).

Kauffman et al., "Detection of DNA Cleavage in Apoptotic Cells," Methods in Enzymol., 322:3-15 (2000).

Kennedy and Schultz, "Mechanism of Association of a Specific Aldehyde "Transition-State Analogue" to the Active Site of α-Chymotrypsin," Biochem. 18:349-356 (1979).

Lorenzo et al., "Cytofluorometric Quantitation of Nuclear Apoptosis Induced in a Cell-Free System," Methods in Enzymol., 322:198-201 (2000).

Mitsiades et al., "Proteomic Analyses in Waldenstrom's Macroglobulinemia and Other Plasma Cell Dyscrasias," Semin. Oncol., 30(2):156-60 (2003).

Mitsiades et al., "The proteasome inhibitor PS-341 potentiates sensitivity of multiple myeloma cells to conventional chemotherapeutic agents: therapeutic applications," Blood 101(6):2377-2380 (2003).

Mitsiades et al., "TRAIL/Apo2L ligand selectively induces apoptosis and overcomes drug resistance in multiple myeloma: therapeutic applications," Blood 98(3):795-804 (2001).

Miura et al., "Transient transfection assay of cell death genes," Methods in Enzymol., 322:480-492 (2000).

Odake et al., "Human and Murine Cytotoxic T Lymphocyte Serine Proteases: Subsite Mapping with Peptide Thioester Substrates and Inhibition of Enzyme Activity and Cytolysis by Isocoumarins," Biochem. 30(8): 2217-2227 (1991).

Orlowski et al., "Substrate Specificity and Inhibitors of a Capillary Injury-Related Protease from Sheep Lung Lumph," Arch. Biochem. and Biophys. 269(1):125-136 (1989).

Orlowski et al., "Evidence for the Presence of Five Distinct Proteolytic Components in the Pituitary Multicatalytic Proteinase Complex. Properties of Two Components Cleaving Bonds on the Carboxyl Side of Branched Chain and Small Neutral Amino Acids," Biochem. 32:1563-1572 (1993).

Orlowski, Marian, "The Multicatalytic Protinease Complex, a Major Extralysosomal Proteolytic System," Biochemistry 29:10289-10297 (1989).

Oweida et al., "In Vivo Determination of the Anticoagulant Effect of a Substituted Isocoumarin (Acitic)," Thrombosis Res. 58(2):191-197 (1990).

Parkes et al., "Calpain inhibition by peptide epoxides," Biochem. J. 230:509-516 (1985).

Powers et al., "Inhibitors of serine proteinases," Proteinase Inhibitors, Barrett and Salvesen (eds), Elsevier, pp. 55-152 (1986).

Powers et al., "Mechanism-Based Isocoumarin Inhibitors for Serine Proteases: Use of Active Site Structure and Substrate Specificity in Inhibitor Design," J. Cell. Biochem. 39(1):33-46 (1989).

Powers et al., "Reaction of Porcine Pancreatic Elastase with 7-Substituted 3-Alkoxy-4-chloroisocoumarins: Design of Potent Inhibitors Using the Crystal Structure of the Complex Formed with 4-Chloro-3-ethoxy-7-guanidinoisocoumarin," Biochem. 29(12):3108-3118 (1990).

Puri et al., "Thrombin-Induced Platelet Aggregation Involves an Indirect Proteolytic Cleavage of Aggregin by Calpain," Arch. Biochem. Biophys., 27(2):346-358 (1989).

Rao et al., "Influence of a Calcium Dependent Protease Inhibitor on Platelet Activation and Secretion," Thromb. Res. 47:625-637 (1987).

Rivett et al., "The Multicatalytic Proteinase of Mammalian Cells," Archs. Biochem. Biophys. 218(1):1-8 (1989).

Rivett et al., "The Multicatalytic Proteinase," J. Biol. Chem. 264(12):12215-12219 (1989).

Rosenquist et al., "Cloning and characterization of a mammalian 8-oxoguanine DNA glycosylase," Proc. Natl. Acad. Sci., 94:7429-7434 (1997).

Sixma, Titia, "DNA mismatch repair: MutS structures bound to mismatches," Curr Opin Struct Biol 11:47-52 (2001).

Tanaka et al., "Proteosomes: Protein and Gene Structures," New Biologist 4(3):173-187 (1992).

Tsujinaka et al., "Synthesis of a new cell penetrating calpain inhibitor (calpeptin)," Biochem. Biophys. Res. Commun., 153:1201-1208 (1988).

Vijayalakshmi et al., "Structural study of procine pancreatic elastase complexed with 7-amino-3-(2-bromoethoxy)-4-chloroisocoumarin as a nonreactivatable doubly covalent enzyme-inhibitor complex," Biochem. 30(8):2175-2183 (1991).

Vinitsky et al., "Inhibition of the chymotrypsin-like activity of the pituitary multicatalytic proteinase complex," Biochem. 31:9421-9428 (1992).

Vlasak et al., "Influenza C Virus Esterase: Analysis of Catalytic Site, Inhibition, and Possible Function," J. Virol. 63(5):2056-2062 (1989).

Zunino et al., "Localization, implications for function, and gene expression of chymotrypsin-like proteinases of cytytoxic RNK-16 lymphocytes," Biochem. et Biophys. Acta 967(3):331-340 (1988).

Hideshima et al., The Proteasome Inhibitor PS-341 Inhibits Growth, Induces Apoptosis, and Overcomes Drug Resistance in Human Multiple Myeloma Cells, Cancer Research, 61(7):3071-3076 (2001).

Ma et al., "The Proteasome Inhibitor PS-341 Markedly Enhances Sensitivity of Multiple Myeloma Tumor Cells to Chemotherapeutic Agents," Clinical Cancer Research, 9:1136-1144 (2003).

Vesole et al., "High-dose melphalan with autotransplantation for refractory multiple myeloma: Results of a southwest oncology group phase II trial," Journal of Clinical Oncology, 17(7):2173-2179 (1999).

Yang et al., "A prospective, open-label safety and efficacy study of combination treatment with bortezomib," Clinical Lymphoma, 4:119-122 (2003).

International Search Report dated May 28, 2004 from PCT/US03/35513.

Supplementary European Search Report dated Apr. 17, 2008 from EP 03 76 8749.

McConkey et al., "Preclinical evaluation of proteasome inhibitor-based combination chemotherapy for advanced prostate cancer," Proceedings of the American Association for Cancer Research Annual Meeting, 42:229-230 (2001).

Thornton et al., "Doxorubicin-induced NF- K B activation in breast cancer is overcome by proteasome inhibition, resulting in enhanced tumoricidal response to treatment," Surgical Forum, 52:200-201 (2001).

* cited by examiner

METHODS AND COMPOSITIONS FOR TREATING CANCER USING PROTEASOME INHIBITORS

RELATED APPLICATIONS

This application claims the benefit of priority under 35 U.S.C. §119 to PCT/US03/035513, which was filed on Nov. 6, 2003, which claims the benefit of U.S. Provisional Application Ser. No. 60/424,363, filed on Nov. 6, 2002, the entire contents of which are incorporated herein by this reference.

GOVERNMENT SUPPORT

Work related to this invention was supported by the National Institutes of Health grant numbers RO-1 50947 and PO-1 78378.

BACKGROUND OF THE INVENTION

Worldwide, cancer is a leading cause of death. Cancers can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals or in the presence of inhibitory signals. In a cancerous or neoplastic state, a cell acquires the ability to "override" these signals and to proliferate under conditions in which a normal cell would not.

Presently, few cures exist for treating the various types of cancer. Among the possible cures that do exist include the application of tumor-inhibiting compounds (chemotherapy), radiation therapy, and bone-marrow transplants. Chemotherapy treatments typically include the application of chemotherapeutic agents to a patient in selected dosages to achieve and maintain a therapeutically effective level of the agents in the patient. However, most known chemotherapeutic agents used for the treatment of cancer display significant side effects. Thus, a drawback of typical chemotherapy treatments is that the compounds employed are non-specific in their activity and accumulate to toxic levels, and hence kill rapidly proliferating normal cells, as well as tumor cells. Furthermore, often a therapeutic agent that is initially effective for a given patient becomes, over time, ineffective or less effective for that patient. Further, a therapeutic agent that is effective, at least initially, for some patients can be completely ineffective or even harmful for other patients.

Accordingly, it would be useful to identify compounds that sensitize cancer cells, to conventional chemotherapy such that the therapeutic effect of any given chemotherapeutic agent is maximized. Such compounds would ideally also reduce the required dosage of the chemotherapeutic agent thereby resulting in fewer side effects in the patient.

SUMMARY OF THE INVENTION

The present invention is based, at least in part, on the discovery that proteasome inhibitors sensitize cancer cells to chemotherapeutic agents. The present invention is further based on the discovery that proteasome inhibitors sensitize cancer cells, even from patients who relapsed after monotherapy, with a proteasome inhibitor, e.g., PS-341. The present invention is also based on the discovery that proteasome inhibitors abolish cell adhesion-mediated drug resistance. The present invention therefore demonstrates that proteasome inhibitors, e.g., PS-341, can induce and/or restore cancer cell sensitivity to therapeutic agents. While not wishing to be bound by theory, it is believed that the proteasome inhibitors can induce and/or restore cancer cell sensitivity to therapeutic agents by down-regulating the expression of apoptosis inhibitors, as well as by inhibiting genotoxic stress response pathways.

Accordingly, in one embodiment, the invention relates to therapeutic compositions for treating cancer or preventing the growth of cancer cells, e.g., tumor growth, in a subject. In another embodiment, the invention relates to therapeutic compositions for treating cancer or preventing the growth of cancer cells in a subject who has become resistant to treatment. The compositions of the present invention include an effective amount of a proteasome inhibitor and an effective amount of a therapeutic agent, e.g., a chemotherapeutic agent, e.g., in a pharmaceutically acceptable carrier. In one embodiment, the effective amount of a proteasome inhibitor is from about 0.001 mg/m$^2$ body surface area/day to about 4.0 mg/m$^2$ body surface area/day.

Other aspects of the invention include packaged proteasome inhibitor(s) and chemotherapeutic agent(s). The packaged compounds and agents also include instructions for using the proteasome inhibitor/chemotherapeutic agent combination for treating cancer or preventing the growth of cancer cells.

In another embodiment, the invention relates to methods for treating cancer, e.g., inhibiting tumor growth, in a subject by administering to a subject an effective amount of a proteasome inhibitor and an effective amount of a therapeutic agent, e.g., a chemotherapeutic agent. The methods of the present invention allow for a reduction in the amount of the therapeutic agent, e.g., a chemotherapeutic agent, required to be effective, resulting in fewer side effects in the subject being treated.

In another embodiment, the invention relates to methods for purging bone marrow, i.e., removing cancer cells from bone marrow, by exposing the bone marrow cells to a proteasome inhibitor and a therapeutic agent, e.g., a chemotherapeutic agent. The purged bone marrow may then be placed back into the subject from whom the bone marrow was removed, or placed into a different subject.

Other features and advantages of the invention will be apparent from the detailed description and from the claims. Materials and methods similar or equivalent to those described herein can be used in the practice or testing of the invention, and are intended to be encompassed by the present invention.

BRIEF DESCRIPTION OF THE FIGURES

FIGS. 1A-1I demonstrate that PS-341 sensitizes multiple myeloma (MM) cells to DNA-damaging chemotherapy. In FIG. 1A, MM.1S cells were pretreated with doxorubicin (40 nM), melphalan (1 μM) or dexamethasone (0.5 μM) for 24 h, and then PS-341 (2 nM) was added for additional 24 h (black bars: without PS-341, white bars: with PS-341).

FIGS. 2A-2D demonstrate that PS-341 inhibits the genotoxic stress response pathways.

DETAILED DESCRIPTION

The present invention relates to the use of a proteasome inhibitor in combination with a therapeutic agent, e.g., a chemotherapeutic agent, for the treatment of cancer. The present invention also relates to methods for treating cancer in a subject by administering to a subject an effective amount of a proteasome inhibitor and an effective amount of a therapeutic agent. The present invention further relates to purging bone marrow by exposing the bone marrow cells to a proteasome inhibitor and a therapeutic agent, i.e., a chemotherapeutic agent.

In order that the present invention may be more readily understood, certain terms are first defined. Additional definitions are set forth throughout the detailed description.

As used herein, the term "proteasome inhibitor" is intended to include inhibitors of the peptidases of the proteasome. More specifically, these inhibitors of the peptidases of the proteasome include inhibitors of the chymotrypsin-like and trypsin-like proteases, in addition to thiol and serine proteases. In addition to antibiotic inhibitors originally isolated from actinomycetes, a variety of peptide aldehydes have been synthesized, such as the inhibitors of chymotrypsin-like proteases described by Siman et al. (WO91/13904). A variety of inhibitors of the proteasome complex have been reported, e.g., Dick, et al., *Biochem.* 30: 2725 (1991); Goldberg, et al., *Nature* 357: 375 (1992); Goldberg, *Eur. J. Biochem.* 203: 9 (1992); Orlowski, *Biochem.* 29: 10289 (1989); Rivett, et al., *Archs. Biochem. Biophys.* 218: 1 (1989); Rivett, et al., *J. Biol. Chem.* 264: 12, 215 (1989); Tanaka, et al., *New Biol.* 4: 1 (1992). Proteasome inhibitors are also discussed in U.S. Pat. No. 5,693,617, the disclosure of which is incorporated herein by reference.

By way of background, proteasomes are large, multienzyme complexes that play a key role in protein breakdown. The average human cell contains about 30,000 proteasomes, each of which contains several protein-digesting proteases. These complexes help regulate a whole host of functions including transcription, viral infection, oncogenesis, cell cycle, stress response, ribosome biogenesis, abnormal protein catabolism, neural and muscular degeneration, antigen processing, DNA repair, and cellular differentiation. Proteasome activity is exquisitely controlled; when it becomes either overzealous (degrading more proteins than it should) or underachieving (neglecting to degrade certain proteins) disease can develop. When the cell needs to destroy a protein, it usually marks it with a chain of small polypeptides called ubiquitin. This structure acts as a ticket into the proteosome's enclosed proteolytic chamber, and the cell stamps this ticket using three enzymatic activities, E1, E2, and E3. The ATP-dependent E1 enzyme activates ubiquitin and links it to the ubiquitin-conjugating enzyme, E2. The E3 enzyme, an ubiquitin ligase, then links the ubiquitin molecule to the protein. This process repeats itself until the doomed polypeptide trails a long chain of ubiquitin moieties; the proteasome finally degrades the protein into small fragments. The ubiquitin-proteasome pathway degrades 90% of all abnormal, misfolded proteins and all of the short-lived, regulatory proteins in the cell. These short-lived proteins, whose half-lives are less than three hours, account for 10% to 20% of all cellular proteins. The pathway also breaks down the bulk of longer-lived proteins. All told, the ubiquitin-proteasome pathway is responsible for degrading 80% to 90% of all the cell's proteins.

In addition to the known proteasome inhibitors, the present invention is intended to encompass other molecules that can be routinely tested for their ability to inhibit proteasome activity. Various strategies for the identification of such inhibitors are exemplified in the art. For example, small molecule libraries, often comprising extracts from plants or more simple organisms, may be screened for their ability to inhibit specific protease types. Alternatively, a rational design approach may be applied using, for example, peptide or peptidomimetic compounds designed specifically to interact with the active site of a proteasome component (see e.g., Siman, et al., WO91/13904; Powers, et al., in Proteinase Inhibitors, Barrett, et al. (eds.), Elsevier, pp. 55-152 (1986)). The inhibitors can be stable analogs of catalytic transition states such as Z-Gly-Gly-Leu-H, which inhibits the chymotrypsin-like activity of the proteasome (Orlowski, *Biochemistry* 29: 10289 (1990); see also Kennedy and Schultz, *Biochem.* 18: 349 (1979)).

In addition, a variety of natural and chemical proteasome inhibitors reported in the literature, or analogs thereof, are intended to be encompassed by the present invention including peptides containing an .alpha.-diketone or an .alpha.-ketone ester, peptide chloromethyl ketone, isocoumarins, peptide sulfonyl fluorides, peptidyl boronates, peptide epoxides, and peptidyl diazomethanes. Angelastro, et al., *J. Med Chem.* 33: 11 (1990); Bey, et al., EPO 363,284; Bey, et al., EPO 363,284; Bey, et al., EPO 364,344; Grubb, et al., WO 88/10266; Higuchi, et al., EPO 393,457; Ewoldt, et al., *Mol. Immunol.* 29(6): 713 (1992); Hernandez, et al., *J. Med. Chem.* 35(6): 1121 (1992); Vlasak, et al., *J. Virol.* 63(5): 2056 (1989); Hudig, et al., *J Immunol.* 147(4): 1360 (1991); Odake, et al., *Biochem.* 30(8): 2217 (1991); Vijayalakshmi, et al., *Biochem.* 30(8): 2175 (1991); Kam, et al., *Thrombosis and Haemostasis* 64(1): 133 (1990); Powers, et al., *J. Cell. Biochem.* 39(1): 33 (1989); Powers, et al., *Proteinase Inhibitors*, Barrett et al., Eds., Elsevier, pp. 55-152 (1986); Powers, et al., *Biochem* 29(12): 3108 (1990); Oweida, et al., *Thrombosis Res.* 58(2): 391 (1990); Hudig, et al., *Mol. Immunol.* 26(8): 793 (1989); Orlowski, et al., *Arch. Biochem. and Biophys.* 269(1): 125 (1989); Zunino, et al., *Biochem. et Biophys. Acta* 967(3): 331 (1988); Kam, et al., *Biochem.* 27(7): 2547 (1988); Parkes, et al., *Biochem. J.* 230: 509 (1985); Green, et al., *J. Biol. Chem.* 256: 1923 (1981); Angliker, et al., *Biochem. J.* 241: 871 (1987); Puri, et al., *Arch. Biochem. Biophys.* 27: 346 (1989); Hanada, et al., Proteinase Inhibitors: Medical and Biological Aspects, Katunuma, et al., Eds., Springer-Verlag pp. 25-36 (1983); Kajiwara, et al., *Biochem. Int.* 15: 935 (1987); Rao, et al., *Thromb. Res.* 47: 635 (1987); Tsujinaka, et al., *Biochem. Biophys. Res. Commun.* 153: 1201 (1988)).

Peptide aldehydes and peptide .alpha.-keto esters containing a hydrophobic residue in the P.sub.1 position tested by Vinitsky, et al. (*Biochem.* 31: 9421 (1992), see also Orlowski, et al., *Biochem.* 32: 1563 (1993)) as potential inhibitors of the chymotrypsin-like activity of the proteasome are also intended to be encompassed by the present invention. Other tripeptides that have been described in the literature include Ac-Leu-Leu-Leu-H, Ac-Leu-Leu-Met-OR, Ac-Leu-Leu-Nle-OR, Ac-Leu-Leu-Leu-OR, Ac-Leu-Leu-Arg-H, Z-Leu-Leu-Leu-H, Z-Arg-Leu-Phe-H and Z-Arg-Ile-Phe-H, where OR, along with the carbonyl of the preceding amino acid residue, represents an ester group, and are intended to be encompassed by the present invention.

The chymotrypsin-like proteases and their inhibitors disclosed by Siman, et al. (WO 01/13904) are also intended to be encompassed by the present invention. These inhibitors have the formula R-A4-A3-A2-Y, wherein R is hydrogen, or an N-terminal blocking group; A4 is a covalent bond, an amino acid or a peptide; A3 is a covalent bond, a D-amino acid, Phe, Tyr, Val or a conservative amino acid substitution of Val; A2 is a hydrophobic amino acid or lysine or a conservative amino acid substitution thereof, or when A4 includes at least two amino acids, A2 is any amino acid; and Y is a group reactive with the active site of said protease. The peptide ketoamides, ketoacids, and ketoesters and their use in inhibiting serine proteases and cysteine proteases disclosed by Powers (WO 92/12140) and the uses for calpain inhibitor compounds and pharmaceutical compositions containing them disclosed by Bartus, et al. (WO 92/1850) are also intended to be encompassed by the present invention.

The following compounds, or analogues thereof, are also contemplated to be used as proteasome inhibitors in the present invention: Calpain Inhibitor I, MG101, Calpain Inhibitor II, Epoxomicin, Fraction I (FrI, Hela), Fraction II (II), clasto-Lactacystin beta-lactone, Lactacystin, MG-115, MG-132, Antiserum to NEDD8, PA28 Activator, 20S Proteasome, Polyclonal Antibody to Proteasome 20S alpha-Type 1 Subunit, Polyclonal Antibody to Proteasome 26S Subunit S10B, Polyclonal Antibody to Proteasome 26S Subunit S2, Polyclonal Antibody to Proteasome 26S Subunit S4, Polyclonal Antibody to Proteasome 26S Subunit S5A, Polyclonal Antibody to Proteasome 26S Subunit S6, Polyclonal Antibody to Proteasome 26S Subunit S6', Polyclonal Antibody to Proteasome 26S Subunit S7, Polyclonal antibody to Proteasome 26S Subunit S8, Polyclonal antibody to Proteasome Activator PA28 Alpha, polyclonal antibody to Proteasome Activator PA28 Gamma, Polyclonal antibody to Proteasome Activator PA700 Subunit 10B, 26S Proteasome Fraction, Proteasome Inhibitor I, Proteasome Inhibitor II, Proteasome Substrate I (Fluorogenic), Proteasome Substrate II (Fluorogenic), Proteasome Substrate III (Fluorogenic), Proteasome Substrate IV (Fluorogenic), S-100 Fraction, SUMO-1/Sentrin-1 (1-101), SUMO-1/Sentrin-1 (1-97), Antiserum to SUMO-1/Sentrin-1, Ubc10, Ubc5b, Ubc5c, Ubc6, Ubc7, Antiserum to Ubc9, Ubc9, UbCH2/E2-14K, UbCH3/Cdc34, UbCH5a, Ubiquitin Activating Enzyme (E1), Ubiquitin Activating Enzyme (E1), Ubiquitin Aldehyde, Ubiquitin Conjugating Enzyme Fractions, Ubiquitin C-terminal Hydrolase, Ubiquitin K48R, Methylated Ubiquitin, GST-Ubiquitin, (His)6 Ubiquitin, Ubiquitin-AMC, Ubiquitin-Sepharose.

A preferred class of proteasome inhibitor is "PS-341" which refers to a boronic acid dipeptide proteasome inhibitor. PS-341 inhibits the activation of the transcription factor NF-κB. PS-341 also down-regulates the expression of several apoptosis inhibitors, induces caspase-dependent apoptosis of drug resistant multiple myeloma (MM) cell lines and patient cells, inhibits MM cell binding to bone marrow stromal cells (BMSCs) and inhibits production of MM growth and survival factors in the bone marrow milieu. In a murine plasmacytoma model, PS-341 inhibits tumor growth in a dose dependent fashion and prolongs host survival. In a Phase II multi-center clinical trial of PS-341 in patients with relapsed, refractory MM, objective responses, including some complete responses, were observed.

As used herein, the term "agent" and "therapeutic agent" is defined broadly as anything that cancer cells, including tumor cells, may be exposed to in a therapeutic protocol. In the context of the present invention, such agents include, but are not limited to, chemotherapeutic agents, such as anti-metabolic agents, e.g., Ara AC, 5-FU and methotrexate, antimitotic agents, e.g., TAXOL, inblastine and vincristine, alkylating agents, e.g., melphalan, BCNU and nitrogen mustard, Topoisomerase II inhibitors, e.g., VW-26, topotecan and Bleomycin, strand-breaking agents, e.g., doxorubicin and DHAD, cross-linking agents, e.g., cisplatin and CBDCA, radiation and ultraviolet light.

As used herein, the term "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al., *The Pharmacological Basis of Therapeutics*, 8th Ed., Sec 12:1202-1263 (1990)), and are typically used to treat neoplastic diseases. The chemotherapeutic agents generally employed in chemotherapy treatments are listed below in Table 1.

TABLE 1

| CLASS | TYPE OF AGENT | NONPROPRIETARY NAMES (OTHER NAMES) |
|---|---|---|
| Alkylating | Nitrogen Mustards | Mechlorethamine ($HN_2$) |
| | | Cyclophosphamide |
| | | Ifosfamide |
| | | Melphalan (L-sarcolysin) |
| | | Chlorambucil |
| | Ethylenimines And Methylmelamines | Hexamethylmelamine Thiotepa |
| | Alkyl Sulfonates | Busulfan |

TABLE 1-continued

| CLASS | TYPE OF AGENT | NONPROPRIETARY NAMES (OTHER NAMES) |
|---|---|---|
| Alkylating | Nitrosoureas | Carmustine (BCNU) |
| | | Lomustine (CCNU) |
| | | Semustine (methyl-CCNU) |
| | | Streptozotocin (streptozotocin) |
| | Triazenes | Decarbazine (DTIC; dimethyltriazenoimi-dazolecarboxamide) |
| | Alkylator | cis-diamminedichloroplatinum II (CDDP) |
| Antimetabolites | Folic Acid Analogs | Methotrexate (amethopterin) |
| | Pyrimidine Analogs | Fluorouracil ('5-fluorouracil; 5-FU) |
| | | Floxuridine (fluorode-oxyuridine; FUdR) |
| | | Cytarabine (cytosine arabinoside) |
| | Purine Analogs and Related Inhibitors | Mercaptopuine (6-mercaptopurine; 6-MP) |
| | | Thioguanine (6-thioguanine; TG) |
| | | Pentostatin (2' - deoxycoformycin) |
| Natural Products | Vinca Alkaloids | Vinblastin (VLB) |
| | | Vincristine |
| | Topoisomerase Inhibitors | Etoposide |
| | | Teniposide |
| | | Camptothecin |
| | | Topotecan |
| | | 9-amino-campotothecin CPT-11 |
| | Antibiotics | Dactinomycin (actinomycin D) |
| | | Adriamycin (Doxorubicin) |
| | | Daunorubicin (daunomycin; rubindomycin) |
| | | Doxorubicin |
| | | Bleomycin |
| | | Plicamycin (mithramycin) |
| | | Mitomycin (mitomycin C) |
| | | TAXOL |
| | | Taxotere |
| | Enzymes | L-Asparaginase |
| | Biological Response Modifiers | Interfon alfa |
| | | interleukin 2 |
| | Platinum Coordination Complexes | cis-diamminedichloroplatinum II (CDDP) |
| | | Carboplatin |
| | Anthracendione | Mitoxantrone |
| | Substituted Urea | Hydroxyurea |
| Miscellaneous Agents | Methyl Hydraxzine Derivative | Procarbazine (N-methylhydrazine, (MIH) |
| | Adrenocortical Suppressant | Mitotane (o,p'-DDD) |
| | | Aminoglutethimide |
| Hormones and Antagonists | Adrenocorticosteroids | Prednisone |
| | | Dexamethasone |
| | Progestins | Hydroxyprogesterone Caproate |
| | | Medroxyprogesterone Acetate |
| | | Megestrol acetate |
| | Estrogens | Diethylstilbestrol |
| | | Ethinyl estradiol |
| | Antiestrogen | Tamoxifen |
| | Androgens | Testosterone propionate |
| | | Fluoxymesterone |
| | Antiandrogen | Flutamide |
| | Gonadotropin-releasing Hormone analog | Leuprolide |

The chemotherapeutic agents used in the present methods can be a single agent or a combination of agents. Preferred combinations will include agents that have different mechanisms of action, e.g., the use of an anti-mitotic agent in combination with an alkylating agent. In a particularly preferred embodiment, the chemotherapeutic agent used in the methods of the present invention is doxorubicin (Adriamycin). In another particularly preferred embodiment, the chemotherapeutic agent used in the methods of the present invention is melphalan.

As used herein, the term "cancer" is intended to encompass a tumor, including both in vitro and in vivo tumors that form in any organ or body part of the subject. Examples of the types of tumors intended to be encompassed by the present invention include those tumors associated with breast cancer, skin cancer, bone cancer, prostate cancer, liver cancer, lung cancer, brain cancer, cancer of the larynx, gallbladder, pancreas, rectum, parathyroid, thyroid, adrenal, neural tissue, head and neck, colon, stomach, bronchi, kidneys. Specifically, the tumors whose growth rate is inhibited by the present invention include basal cell carcinoma, squamous cell carcinoma of both ulcerating and papillary type, metastatic skin carcinoma, osteosarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcomas, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

In a preferred embodiment, the tumor is multiple myeloma. As used herein, the term "multiple myeloma" refers to a malignancy of the bone marrow in which cancerous plasma cells grow out of control and create a tumor. When these tumors grow in multiple sites, they are referred to as multiple myeloma. Normally, plasma cells make up less than five percent of the cells in bone marrow, but people with multiple myeloma have anywhere from ten percent to more than ninety percent. The overgrowth of malignant plasma cells in bone marrow can cause a number of serious problems throughout the body. Over time, the abnormal cells can permeate the interior of the bone and erode the bone cortex (outer layer). These weakened bones are more susceptible to bone fractures, especially in the spine, skull, ribs, and pelvis As used herein, the term "cancer cell" is intended to include tumor cells, and refers to cells that divide at an abnormal (increased) rate. Cancer cells include, but are not limited to, carcinomas, such as squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma, cholangiocarcinoma, papillary carcinoma, transitional cell carcinoma, choriocarcinoma, semonoma, embryonal carcinoma, mammary carcinomas, gastrointestinal carcinoma, colonic carcinomas, bladder carcinoma, prostate carcinoma, and squamous cell carcinoma of the neck and head region; sarcomas, such as fibrosarcoma, myxosarcoma, liposarcoma, chondrosarcoma, osteogenic sarcoma, chordosarcoma, angiosarcoma, endotheliosarcoma, lymphangiosarcoma, synoviosarcoma and mesotheliosarcoma; leukemias and lymphomas such as granulocytic leukemia, monocytic leukemia, lymphocytic leukemia, malignant lymphoma, plasmocytoma, reticulum cell sarcoma, or Hodgkins disease; and tumors of the nervous system including glioma, meningoma, medulloblastoma, schwannoma or epidymoma.

As used herein, the term "inhibiting cancer cell growth" is intended to include the inhibition of undesirable or inappropriate cell growth. The inhibition is intended to include inhibition of proliferation including rapid proliferation. The term "inhibiting cancer cell growth" is also intended to encompass inhibiting tumor growth which includes the prevention of the growth of a tumor in a subject or a reduction in the growth of a pre-existing tumor in a subject. The inhibition also can be the inhibition of the metastasis of a tumor from one site to another. A cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

A cancer cell is "sensitive" to a therapeutic agent if its rate of growth is inhibited as a result of contact with a therapeutic agent, compared to its growth in the absence of contact with the therapeutic agent. The quality of being sensitive to a therapeutic agent is a variable one, with different cancer cells exhibiting different levels of "sensitivity" to a given therapeutic agent, under different conditions.

A cancer cell is "resistant" to a therapeutic agent if its rate of growth is not inhibited, or inhibited to a very low degree, as a result of contact with the therapeutic agent when compared to its growth in the absence of contact with the therapeutic agent. The quality of being resistant to a therapeutic agent is a highly variable one, with different cancer cells exhibiting different levels of "resistance" to a given therapeutic agent under different conditions.

Determination of whether a patient is "sensitive" or "resistant" to a therapeutic agent and/or protocol can be readily made by the physician (the "attending clinician"), as one skilled in the art, by the use of known techniques. For example, a number of factors are considered by the attending clinician, including, but not limited to: the specific cancer involved; pharmacodynamic characteristics of the particular therapeutic agent; the size, age, and general health of the patient; the degree of or involvement or the severity of the cancer; the particular compound administered; the mode of administration; and other relevant circumstances.

The term "administering" is intended to include routes of administration which allow the proteasome inhibitor and/or therapeutic agent to perform their intended functions of treating cancer or inhibiting cancer cell growth. Examples of routes of administration which can be used include injection (subcutaneous, intravenous, parenterally, intraperitoneally, intrathecal, etc.), oral, inhalation, and transdermal. The injection can be bolus injections or can be continuous infusion. Depending on the route of administration, the proteasome inhibitor or therapeutic agent can be coated with or disposed in a selected material to protect it from natural conditions which may detrimentally affect its ability to perform its intended function. The proteasome inhibitor and/or therapeutic agent can be administered alone, or in conjunction with a pharmaceutically acceptable carrier. Further the proteasome inhibitor and/or therapeutic agent can be administered as a mixture of proteasome inhibitor and/or therapeutic agent, which also can be coadministered with a pharmaceutically acceptable carrier. The proteasome inhibitor and/or therapeutic agent also can be administered as a prodrug which is converted to its active form in vivo.

The language "effective amount" of the combination of the proteasome inhibitor and the therapeutic agent is that amount necessary or sufficient to treat cancer or to inhibit the growth of cancer cells, e.g. prevent the undesirable cell growth, or reduce the size of a pre-existing benign cell mass or malignant tumor in the subject. The effective amount can vary depending on such factors as the type of cell growth being treated or inhibited, the type of therapeutic agent(s) employed, the particular proteasome inhibitor, the size of the subject, or the severity of the cancer cell growth or tumor. For example, the choice of each of the individual agents (proteasome inhibitor or chemotherapeutic agent) which make up the combination can affect what constitutes an "effective amount". One of ordinary skill in the art would be able to study the aforementioned factors and make the determination regarding the effective amount of the combination of the proteasome inhibitor or therapeutic agent without undue experimentation.

For example, an in vitro assay can be used to determine an "effective amount" of the combination of the proteasome inhibitor and a chemotherapeutic agent. The ordinarily skilled artisan would select an appropriate amount of each individual agent in the combination for use in the aforementioned in vitro assay. The cell survival fraction can be used to determine whether the selected amounts were an "effective amount" for the particular combination of agents. For example, the selected amounts used within the assay preferably should result in a killing of at least 50% of the cells, more preferably 75%, and most preferably at least 95%. In a preferred embodiment, the effective dose of the proteasome inhibitor and the therapeutic agent is a subtoxic dose. As used herein, the term subtoxic dose refers to a dose which results in the killing of less than about 10% of the cells. In one embodiment, the effective dose of a proteasome inhibitor is from about 0.001 mg/m$^2$ body surface area/day to about 4.0 mg/m$^2$ body surface area/day. In another embodiment, the effective dose of a proteasome inhibitor is from about 0.001 mg/m$^2$ body surface area/day to about 0.01 mg/m$^2$ body surface area/day. In another embodiment, the effective dose of a proteasome inhibitor is from about 0.01 mg/m$^2$ body surface area/day to about 0.1 mg/m$^2$ body surface area/day. In a further embodiment, the effective dose of a proteasome inhibitor is from about 0.1 mg/m$^2$ body surface area/day to about 2.0 mg/m$^2$ body surface area/day. In yet a further embodiment, the effective dose of a proteasome inhibitor is from about 0.1 mg/m$^2$ body surface area/day to about 1.7 mg/m$^2$ body surface area/day.

The regimen of administration can also affect what constitutes an effective amount. The proteasome inhibitor can be administered to the subject prior to, simultaneously with, or after the administration of the therapeutic agent. Further, several divided dosages, as well as staggered dosages, can be administered daily or sequentially, or the dose can be continuously infused. Further, the dosages can be proportionally increased or decreased as indicated by the exigencies of the therapeutic situation.

The term "regimen of administration" refers to the timing of administration and the sequence of administration of the proteasome inhibitor and the therapeutic agent which allow the proteasome inhibitor and/or therapeutic agent to perform their intended functions of treating cancer or inhibiting cancer cell growth. The regimen of administration, e.g., the timing and/or sequence of administration, of the proteasome inhibitor and/or the therapeutic agent can vary depending on such factors as the pharmacokinetics of the proteasome inhibitor employed, the pharmacokinetics of therapeutic agent used, the type of cell growth being treated or inhibited, the size of the subject, the severity of the cancer cell growth or tumor, or effective dosage. The choice of each of the individual agents (proteasome inhibitor and/or therapeutic agent) which make up the combination can affect what constitutes a "regimen of administration". For example, in embodiments where contacting a cell with a proteasome inhibitor after the cell is contacted with a therapeutic agent is desirable, a proteasome inhibitor with slower pharmacokinetics may be administered prior to the administration of the therapeutic agent such that the proteasome inhibitor contacts the cell subsequent to contact with the therapeutic agent. Proteasome inhibitors with rapid pharmacokinetics may be administered after the therapeutic agent such that the proteasome inhibitor contacts the cell subsequent to contact with the therapeutic agent. One of ordinary skill in the art would be able to review the aforementioned factors as well as art known proteasome inhibition studies in determining an appropriate regimen of administration of the proteasome inhibitor and/or therapeutic agent without undue experimentation.

As used herein, the term "subject" includes warm-blooded animals, preferably mammals, including humans. In a preferred embodiment, the subject is a primate. In an even more preferred embodiment, the subject is a human.

I. Methods of the Invention

The methods of the invention relate to therapeutic and prophylactic compositions for treating cancer or preventing the growth of cancer cells, e.g., tumor growth, in a subject. The compositions of the present invention include an effective amount of a proteasome inhibitor and an effective amount of a therapeutic agent, e.g., a chemotherapeutic agent, e.g., in a pharmaceutically acceptable carrier. Other aspects of the invention include packaged proteasome inhibitor(s) and chemotherapeutic agent(s). The packaged compounds and agents also include instructions for using the proteasome inhibitor/chemotherapeutic agent combination for treating cancer or preventing the growth of cancer cells.

In another aspect, the invention relates to methods for treating cancer, e.g., inhibiting tumor growth, in a subject by administering to a subject an effective amount of a proteasome inhibitor and an effective amount of a therapeutic agent, e.g., a chemotherapeutic agent. The methods of the present invention allow for a reduction in the amount of the therapeutic agent, e.g., a chemotherapeutic agent, required to be effective, resulting in fewer side effects in the subject being treated.

In yet another aspect, the invention relates to methods for purging bone marrow, i.e., removing cancer cells from bone marrow, by exposing the bone marrow cells to a proteasome inhibitor and a therapeutic agent, e.g., a chemotherapeutic agent. The purged bone marrow may then be placed back into the subject from which the bone marrow was removed, or placed into a different subject.

In general, the methods of the invention include a step of contacting cancer cells with a combination of a proteasome inhibitor and a therapeutic agent, e.g., a chemotherapeutic agent, effective for promoting apoptosis or cell death. In one embodiment, the proteasome inhibitor and the therapeutic agent are packaged. In another embodiment, the effective amount of a proteasome inhibitor is from about 0.001 mg/m$^2$ body surface area/day to about 4.0 mg/m$^2$ body.

As used herein, the term "cell death" includes the processes by which mammalian cells die or become terminally differentiated. Such processes include apoptosis (both reversible and irreversible) and processes thought to involve apoptosis (e.g., cell senescence), as well as necrosis and terminal cell differentiation. "Cell death" is used herein to refer to the death or imminent death of nucleated cells (e.g., neurons, myocytes, hepatocytes and the like) as well as to the death or imminent death of anucleate cells (e.g., red blood cells, platelets, and the like). Cell death is typically manifested by the exposure of the internal membrane phospholipid phosphatidylserine (PS) on the outer leaflet of the plasma membrane and can be detected by art recognized methods.

As used herein the term "apoptosis" includes programmed cell death which can also be detected using techniques which are known in the art. For example, apoptotic cell death can be characterized, e.g., by cell shrinkage, membrane blebbing and chromatin condensation culminating in cell fragmentation. Cells undergoing apoptosis also display a characteristic pattern of internucleosomal DNA cleavage. Apoptosis can be measured in the presence or the absence of Fas-mediated signals. In one embodiment, cytochrome C release from mitochondria during cell apoptosis can be detected, e.g., plasma cell apoptosis (as described in, for example, Bossy-Wetzel. E., et al. (2000) *Methods in Enzymol.* 322:235-42). Other assays include: cytofluorometric quantitation of nuclear apoptosis induced in a cell-free system (as described in, for example, Lorenzo, H. K., et al. (2000) *Methods in Enzymol.* 322:198-201); apoptotic nuclease assays (as described in, for example, Hughes, F. M. (2000) *Methods in Enzymol.* 322:47-62); analysis of apoptotic cells, e.g., apoptotic plasma cells, by flow and laser scanning cytometry (as described in, for example, Darzynkidewicz, Z., et al. (2000) *Methods in Enzymol.* 322:18-39); detection of apoptosis by annexin V labeling (as described in, for example, Bossy-Wetzel, E., et al. (2000) *Methods in Enzymol* 322:15-18); transient transfection assays for cell death genes (as described in, for example, Miura, M., et al. (2000) *Methods in Enzymol.* 322:480-92); and assays that detect DNA cleavage in apoptotic cells, e.g., apoptotic plasma cells (as described in, for example, Kauffman, S. H., et al. (2000) *Methods in Enzymol.* 322:3-15). Apoptosis can also be measured by propidium iodide staining or by TUNEL assay.

In another aspect, the invention features methods for inhibiting the proliferation of cancer cells by contacting the cells with a proteasome inhibitor and a therapeutic agent. In general, the method includes a step of contacting cancer cells with a proteasome inhibitor and a therapeutic agent effective for reducing the proliferation of cancer cells. The reduced proliferation of cancer cells can be detected by at least one of the following biological activities: (1) a decrease in solid tumor cell proliferation; (2) a decrease in the fraction of cells in the DNA synthesis phase of the cell cycle (S-phase); (3) an increase in expression of differentiation-associated markers; (4) a decrease in the expression of proliferation-associated markers such as Ki-67 (MIB-1), e.g., a decrease in the expression of Ki-67 by about 30-50%, using techniques which are known in the art. Changes in expression can occur in the protein or mRNA levels.

The present method can be performed on cells in culture, e.g., ex vivo, or can be performed on cells present in an animal subject, e.g., as part of an in vivo therapeutic protocol. The therapeutic regimen can be carried out on a human or other animal subject.

The methods of the present invention allow for a reduction in the amount of the therapeutic agent, e.g., a chemotherapeutic agent, required to be effective, resulting in fewer side effects in the subject being treated.

In one embodiment, the cells to be treated are multiple myeloma cells. For instance, the instant method can be carried out to prevent the proliferation of a multiple myeloma cell tumor. As used herein, the term "multiple myeloma"

refers to a malignancy of the bone marrow in which cancerous plasma cells grow out of control and create a tumor. When these tumors grow in multiple sites, they are referred to as multiple myeloma.

Particular examples of chemotherapeutic agents include anti-tumor substances such as: mitotic inhibitors, such as vinblastine; alkylating agents, such as cisplatin, carboplatin and cyclophosphamide; antimetabolites, such as 5-fluorouracil, cytosine arabinoside, hydroxyurea or N-[5-[N-(3,4-dihydro-2-methyl-4-oxoquinazolin-6-ylmethyl)-N-methylamino]-2-thenoyl]-L-glutamic acid; intercalating antibiotics, as for example adriamycin and bleomycin; enzymes, such as asparaginase; topoisomerase inhibitors, such as etoposide; biological response modifiers, e.g., to enhance anti-tumor responses, such as interferon; apoptotic agents, such as actinomycin D; and anti-hormones, for example antioestrogens such as tamoxifen or, for example antiandrogens such as 4'-cyano-3-(4-fluorophenylsulphonyl)-2-hydroxy-2-methyl-3'-(trifluoromethyl) propionanilide. Other examples of chemotherapeutic agents include those listed in Table 1.

Determination of a therapeutically effective amount of a proteasome inhibitor and a therapeutically effective amount of a therapeutic agent, e.g., a chemotherapeutic agent, can be readily made by the physician (the "attending clinician"), as one skilled in the art, by the use of known techniques and by observing results obtained under analogous circumstances. The dosages may be varied depending upon the requirements of the patient in the judgment of the attending clinician, the severity of the condition being treated and the particular compound being employed. In determining the therapeutically effective amount or dose, a number of factors are considered by the attending clinician, including, but not limited to: the specific hyperplastic/neoplastic cell involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment; and other relevant circumstances. U.S. Pat. No. 5,427,916, for example, describes method for predicting the effectiveness of antineoplastic therapy in individual patients, and illustrates certain methods which can be used in conjunction with the treatment protocols of the instant invention.

Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

A therapeutically effective amount of a proteasome inhibitor is expected to be from about 0.001 milligram per meter squared body surface area pet day (mg/m$^2$ body surface area/day) to about 4 mg/m$^2$ body surface area/day. A therapeutically effective amount of a chemotherapeutic agent is and may be determined using art-recognized methods.

The effectiveness of any particular combination of a proteasome inhibitor with a chemotherapeutic agent to treat cancer can be monitored by comparing two or more samples obtained from a patient undergoing anti-cancer treatment. In general, it is preferable to obtain a first sample from the patient prior to beginning therapy and one or more samples during treatment. In such a use, a baseline of expression of cancer cells prior to therapy is determined and then changes in the baseline state of expression of cancer cells is monitored during the course of therapy. Alternatively, two or more successive samples obtained during treatment can be used without the need of a pre-treatment baseline sample. In such a use, the first sample obtained from the subject is used as a baseline for determining whether the expression of cancer cells is increasing or decreasing.

In general, when monitoring the effectiveness of a therapeutic treatment, two or more samples from the patient are examined. Preferably, three or more successively obtained samples are used, including at least one pretreatment sample.

II. Pharmaceutical Compositions

In another aspect, the present invention provides pharmaceutically acceptable compositions which comprise a therapeutically-effective amount of a proteasome inhibitor and/or therapeutic agent, e.g., a chemotherapeutic agent, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of a combination of a proteasome inhibitor and a chemotherapeutic agent, or composition comprising a combination of a proteasome inhibitor and a chemotherapeutic agent which is effective for producing some desired therapeutic effect, e.g., by inhibiting the proliferation and/or inducing the differentiation of at least a sub-population of cells in an animal at a reasonable benefit/risk ratio applicable to any medical treatment.

The phrase "pharmaceutically acceptable" is employed herein to refer to those combinations of a proteasome inhibitor and a chemotherapeutic agent, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the proteasome inhibitors and/or the chemotherapeutic agents encompassed by the invention. These salts can be prepared in situ during the final isolation and purification of the proteasome inhibitors or the chemotherapeutic agents, or by separately reacting purified proteasome inhibitors or the chemotherapeutic agents in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge, et al. (1977) "Pharmaceutical Salts", *J. Pharm. Sci.* 66:1-19)

In other cases, the proteasome inhibitors or the chemotherapeutic agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of proteasome inhibitors or chemotherapeutic agents. These salts can likewise be prepared in situ during the final isolation and purification of the proteasome inhibitors or the chemotherapeutic agents, or by separately reacting the purified proteasome inhibitor or the chemotherapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge, et al., supra).

Wetting agents, emulsifiers and lubricants, such as sodium lauryl sulfate and magnesium stearate, as well as coloring agents, release agents, coating agents, sweetening, flavoring and, perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a proteasome inhibitor or a chemotherapeutic agent with the carrier and, optionally, one or more accessory ingredients. In general, the formulations are prepared by uniformly and intimately bringing into association a proteasome inhibitor or a chemotherapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a proteasome inhibitor or a chemotherapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active proteasome inhibitor and/or the chemotherapeutic agents may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more proteasome inhibitors and/or chemotherapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent. Formulations which are suitable for vaginal administration also include pessaries, tampons, creams, gels, pastes, foams or spray formulations containing such carriers as are known in the art to be appropriate.

Dosage forms for the topical or transdermal administration of a proteasome inhibitor and/or a chemotherapeutic agent include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a proteasome inhibitor and/or a chemotherapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a proteasome inhibitor and/or a chemotherapeutic agent, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The proteasome inhibitor and/or chemotherapeutic agent can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a proteasome inhibitor and/or a chemotherapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more proteasome inhibitors and one or more chemotherapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of a proteasome inhibitor and a chemotherapeutic agent in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the proteasome inhibitors and chemotherapeutic agent of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

EXAMPLES

The following methodology described in the Materials and Methods section was used throughout the in vitro and/or in vivo examples set forth below.

Materials and Methods
Tissue Culture

Human MM cell lines included MM.1S, RPMI-8226/S and its doxorubicin-(Dox40) and melphalan (LR5)-resistant sublines, ARP-1, S6B45, NCI-H929 (American Type Culture Collection, Manassas, Va.) and INA6 (a gift from Renate Burger, University of Erlangen-Nuernberg, Germany). Tumor cells were freshly isolated from the bone marrow of MM patients.

Case Report

A 58 year-old female, with relapsed refractory IgG lambda MM, had received prior therapy with melphalan and prednisone; vincristine, adriamycin (doxorubicin), dexamethasone (VAD) plus cyclophosphamide; high dose melphalan and autologous stem cell transplant; alpha-interferon; and thalidomide. After informed consent, she received cyclic PS-341, 1.3 mg/m$^2$ IV twice a week for 2 weeks with one week off, per Institutional Review Board (IRB) approved protocol. Although serum paraprotein decreased from 5.1 gm/dL to 3.3 gm/dL after 3 cycles of PS-341, she developed fatigue and exacerbation of a pre-existing peripheral neuropathy. PS-341 dose was therefore reduced to 1 mg/m$^2$ and she completed 4 cycles of therapy. Due to progressive disease evidenced by increasing paraprotein (5.0 gm/dL) and circulating plasma cells, dexamethasone (40 mg twice a week for 2 weeks each cycle) was added. Although her tumor burden, as assessed by measurements of the peripheral blood levels of tumor-produced monoclonal protein (M-component), slightly decreased to 4.7 gm/dL and circulating plasma cells transiently cleared, she developed rapidly progressive disease, with 48% circulating plasma cells after the 6th cycle; PS-341 protocol treatment was discontinued. Subsequent therapy with IV cyclophosphamide; thalidomide; thalidomide alone, dexamethasone and biaxin; as well as Doxil (liposomal doxorubicin) with thalidomide and dexamethasone, was ineffective. At this time, MM cells were isolated by bone marrow (BM) aspiration and purified as previously described (Mitsiades, C. S., et al. *Blood* 98:795, 2001).

Materials

PS-341 was provided by Millennium Pharmaceuticals (Cambridge, Mass.). MTT, dexamethasone, doxorubicin, and melphalan were obtained from Sigma Chemical Co. (St. Louis, Mo.).

Ku 70 and 80 antibodies were acquired from Lab Vision Corporation (Fremont Calif.).

Methods

RNA isolation, gene expression profiling and data analysis were performed as previously described. High-throughput global proteomic analysis of the signaling state of PS-341-treated MM cells was performed by multiplex-immunoblotting arrays using, for example, the KPKS-1.0 and KPSS-1.0 platforms, as previously described (Mitsiades, N., et al. *Blood.* 2003 Mar. 15; 101(6):2377-80 and Mitsiades, C. S., et al. *Semin Oncol.* 2003 April; 30(2):156-60). Immunoblotting analysis and quantification of cell survival with the 3-(4,5-Dimethylthiazol-2-yl)-2,5-Diphenyltetrazolium Bromide (MTT) assay were performed as previously described.

All experiments were repeated at least three times, and each experimental condition was repeated at least in quadruplicate wells. Results from representative experiments are shown. LD50 values were calculated using the SPSS-11.0 statistical package. Statistical significance was examined by a 2-way analysis of variance, followed by Duncan's posthoc test. In all analyses, p<0.05 was considered statistically significant.

Example 1

Figure 1A:
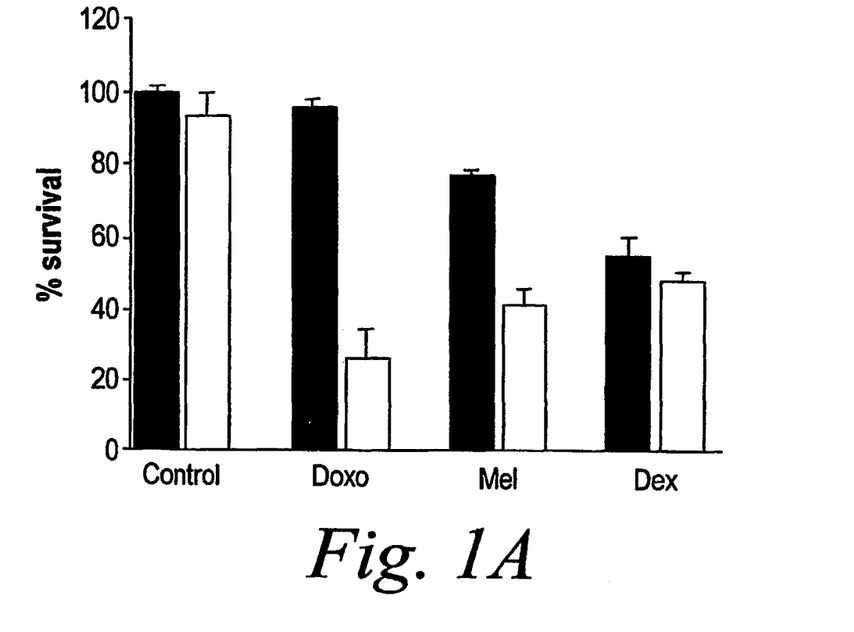

Subtoxic Concentrations of PS-341 Enhance Sensitivity of Cancer Cells to Chemotherapeutic Agents MM.1S cells were pretreated with doxorubicin (40 nM), melphalan (1 μM) or dexamethasone (0.5 μM) for 24 h, and then PS-341 (2 nM) was added for an additional 24 hours. As shown in FIG. 1A, PS-341, at a subtoxic concentration, markedly enhances sensitivity of MM.1S cells to subtoxic concentrations of doxorubicin and to melphalan (P<0.001 in both cases) (black bars: without PS-341, white bars: with PS-341). Thus, PS-341 sensitizes MM.1S cells to DNA-damaging chemotherapy.

However, the subtoxic concentration of PS-341 did not increase the anti-MM effect of dexamethasone (P>0.05). Thus, only additive cytotoxicity exists between PS-341 and dexamethasone.

Example 2

PS-341 Decreases the LD50 of Doxorubicin

Figure 1B:
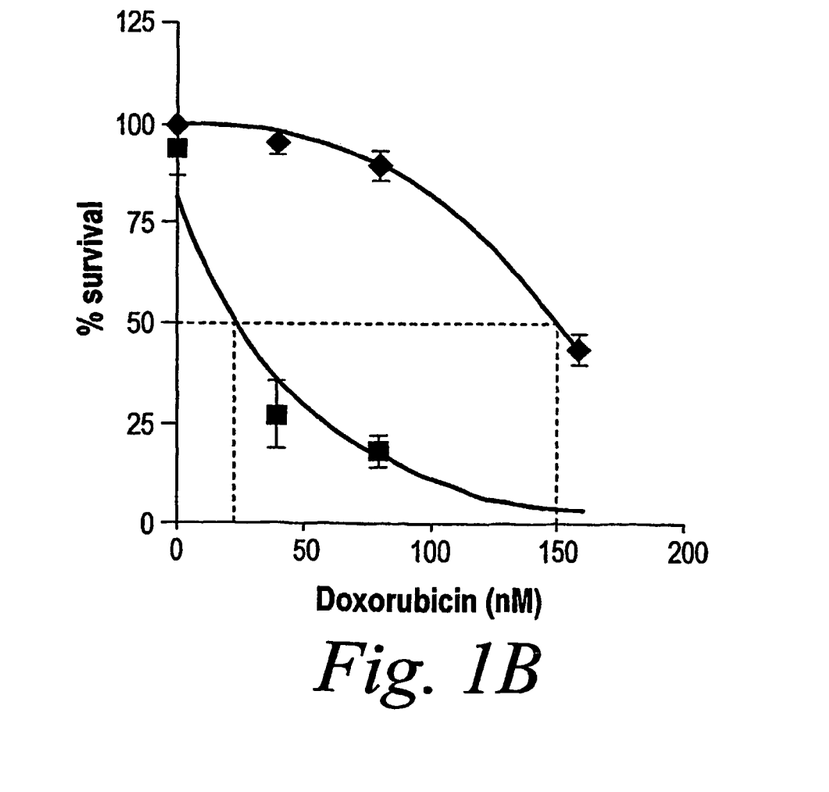
FIG. 1B illustrates a dose-response analysis for the effect of doxorubicin on MM.1S cells in the presence (squares) or absence (diamonds) of PS-341 (2 nM) and reveals that PS341 decreases the LD50 of doxorubicin from 150 to 26 nM.

Dose-response analysis for the effect of doxorubicin on MM.1S cells in the presence or absence of PS341 (2 nM) was performed. As shown in FIG. 1B, the LD50 for doxorubicin in MM.1S cells was 150 nM in the absence and 26 nM in the presence of PS-341 (2 nM). Thus, PS-341 decreases the LD50 of doxorubicin from 150 to 26 nM. The concentration of PS-341 is 10-30 nM in patients' serum, with peaks of 100 nM, which is sufficient to achieve this synergistic effect in vivo.

Example 3

Figure 1C:
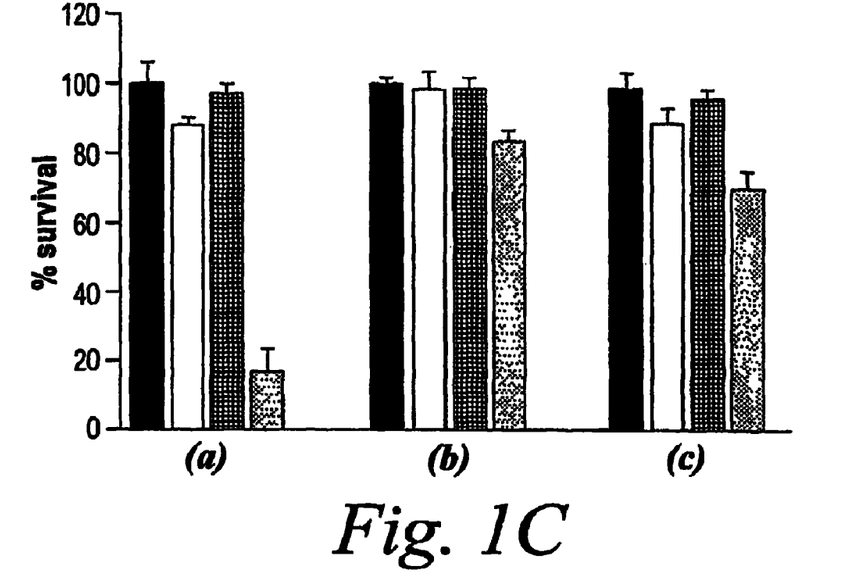
FIG. 1C illustrates a study where MM.1S cells were pretreated with doxorubicin (50 ng/ml) for 24 h and then PS-341 (2 nM) was added for an additional 24 h (a); or pre-treated with PS-341 for 24 h and then doxorubicin for an additional 24 h (b); or treated with PS-341 and doxorubicin together for 24 h (c) (black bars: control, white bars:doxorubicin alone, grid bars: PS-341, gray bars: doxorubicin plus PS-341).

The Sequence of Administration of Doxorubicin and PS-341 Impacts Their Synergistic Anti-MM Effect Whether the sequence of administration of doxorubicin and PS-341 impacts their synergistic anti-MM effect was studied. The following experiments were performed. MM.1S cells were (a) pre-treated with doxorubicin (50 ng/ml) for 24 h and then PS-341 (2 nM) was added for an additional 24 h; or (b) pre-treated with PS-341 for 24 h and then doxorubicin for an additional 24 h; or (c) treated with PS-341 and doxorubicin together for 24 h. As shown in FIG. 1C, although the combination of PS-341 and doxorubicin was more potent than either drug alone under any of these conditions (P<0.05 in all cases), the most pronounced synergy was observed when MM cells are pre-treated with doxorubicin followed by PS-341. Thus, in all cases a synergistic effect is found, but the strongest synergy is observed when the cells are pretreated with doxorubicin followed by PS-341 treatment.

Example 4

PS-341 Sensitizes all MM Cell Lines to Chemotherapy

Figure 1D:
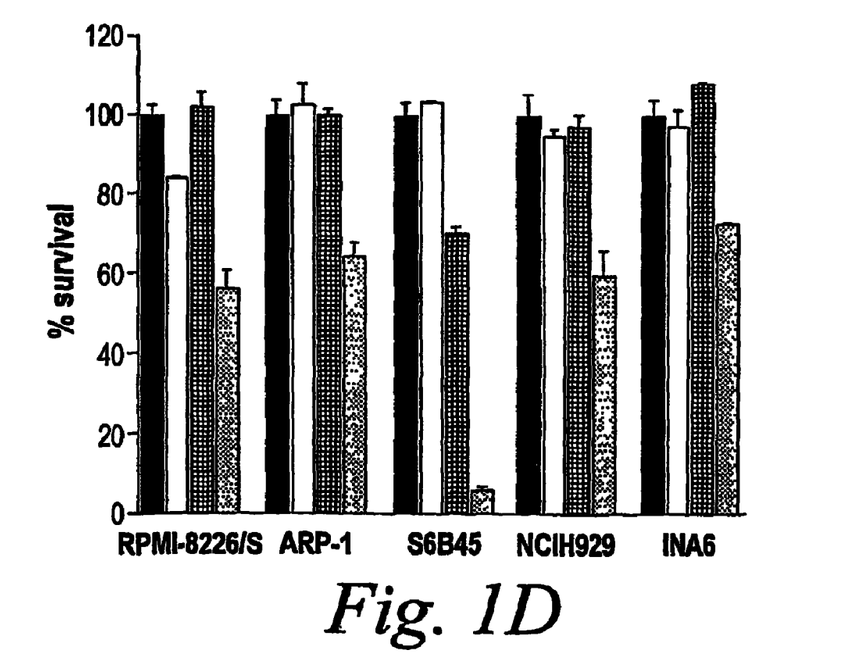
FIG. 1D illustrates a study where RPMI-8226/S, ARP-1, S6B45, NCH-H929 and INA6 cells were pretreated with doxorubicin (50 ng/ml) for 24 h, and then with PS-341 (2 nM) for an additional 24 h (black bars: control, white bars: doxorubicin alone, grid bars: PS-341, gray bars: doxorubicin plus PS-341).

Whether PS-341 sensitizes all MM cell lines to chemotherapy was studied. RPMI-8226/S, ARP-1, S6B45, NCI-11929 and 1NA6 cells were pretreated with doxorubicin (50 ng/ml) for 24 h, and then with PS-341 (2 nM) for an additional 24 h. As shown in FIG. 1D, PS-341 sensitizes all MM cell lines to chemotherapy.

Example 5

PS-341 Sensitizes Primary Patient MM Cells to Doxorubicin

Figure 1E:
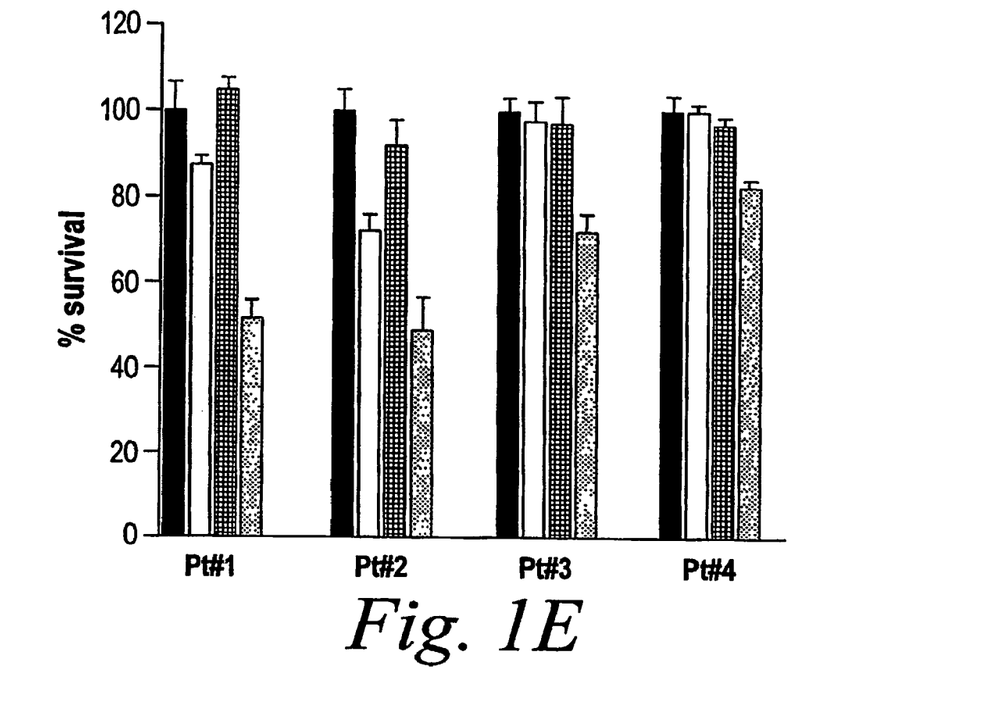
FIG. 1E illustrates a study where primary MM cells from 4 PS-341-naive patients were pretreated with doxorubicin (50 ng/ml) for 24 h, and then with PS-341 (2 nM) for an additional 24 h. (black bars: control, white bars: doxorubicin alone, grid bars: PS-341, gray bars: doxorubicin plus PS-341).

Whether PS-341 sensitizes primary MM cells from PS-341-naïve patients was studied. Primary MM cells from PS-341-naive patients were pretreated with doxorubicin (50 ng/ml) for 24 h, and then with PS-341 (2 nM) for an additional 24 h. As shown in FIG. 1E, PS-341 sensitizes primary patient MM cells to doxorubicin.

Example 6

Figure 1F:
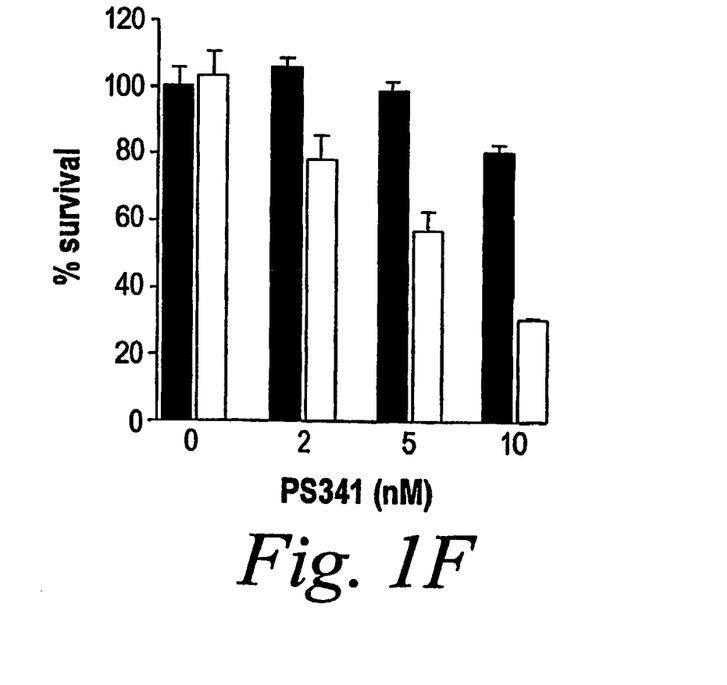
FIG. 1F illustrates a study where doxorubicin-resistant RPMI-Dox40 cells were pretreated with (white bars) or without (black bars) doxorubicin (800 ng/ml) for 24 h, and then PS-341 (2-10 nM) was added for an additional 24 h (black bars: without doxorubicin, white bars: with doxorubicin).

PS-341 Increases Chemo-Sensitivity in Both Doxorubicin Drug-Sensitive and Drug-Resistant MM Cells Whether PS-341 sensitizes cells that have been selected for resistance to doxorubicin was studied. Doxorubicin-resistant RPMI-Dox40 cells were pretreated with or without doxorubicin (800 ng/ml) for 24 h, and then PS-341 (2-10 nM) was added for an additional 24 h. As shown in FIG. 1F, PS-341 sensitizes RPMI-Dox40 cells to doxorubicin. Thus, importantly, the same sensitizing effect is observed in cells that have been selected for resistance to doxorubicin indicating that PS-341 increases chemo-sensitivity in both drug-sensitive and drug-resistant MM cells.

Example 7

Figure 1G:
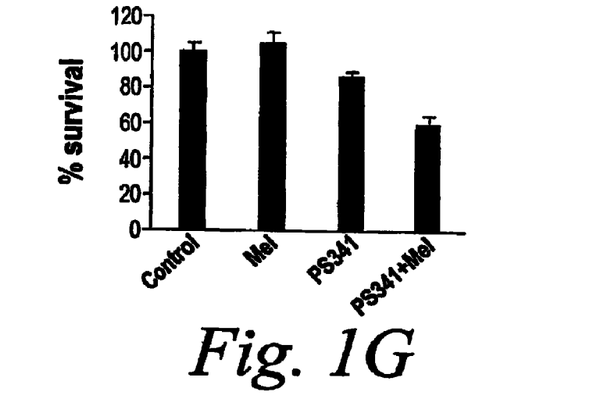
FIG. 1G illustrates a study where melphalan-resistant LR5 cells were pretreated with or without melphalan (5 µM) for 24 h, and then PS-341 (2 nM) was added for an additional 24 h.

PS-341 Increases Chemo-Sensitivity in Both Mephalan Drug-Sensitive and Drug-Resistant MM Cells Whether PS-341 sensitizes cells that have been selected for resistance to melphalan was studied. Melphalan-resistant LR5 cells were pretreated with or without melphalan (5 µM) for 24 h, and then PS-341 (2 nM) was added for an additional 24 h. As shown in FIG. 1G, PS-341 sensitizes LR5 cells to melphalan. Thus, importantly, the same sensitizing effect is observed in cells that have been selected for resistance to melphalan, further indicating that PS-341 increases chemo-sensitivity in both drug-sensitive and drug-resistant MM cells.

Example 8

Figure 1H:
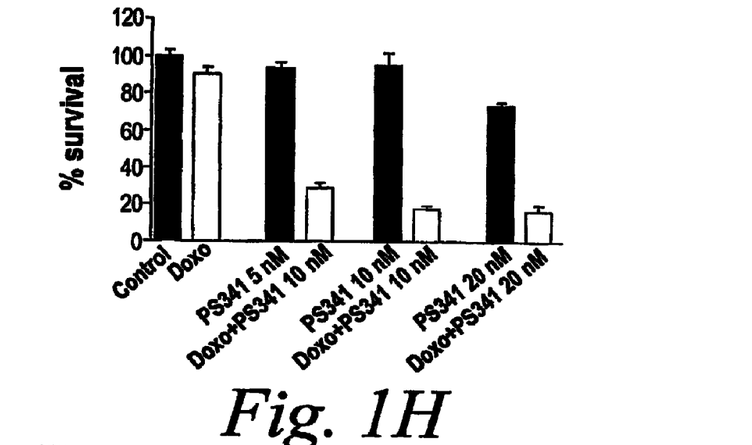
FIG. 1H illustrates a study where MM cells isolated from a patient who had relapsed following treatment with PS-341 were pretreated with (white bars) or without (black bars) doxorubicin (100 ng/ml) for 24 h, and then PS-341 (5-20 nM) was added for an additional 24 h.

Synergy Between PS-341 and Chemotherapy can Reverse Resistance to Chemotherapeutic Agents The effect of PS-341 on the chemosensitivity of primary MM cells isolated from a patient who had relapsed following conventional and high dose chemotherapy, including, interferon-γ therapy, thalidomide alone or in combination with cytotoxic drugs or steroids, liposomal doxorubicin, and PS-341 alone or in combination with dexamethasone was studied. MM cells isolated from a patient who had relapsed following treatment with PS-341 were pretreated with or without doxorubicin (100 ng/ml) for 24 h, and then PS-341 (5-20 nM) was added for an additional 24 h. The MM cells of these patients have low sensitivity to either PS-341 (IC50 of >50 nM compared to IC50<5 nM in PS-341-sensitive patient MM cells) or doxorubicin monotherapy in vitro. However, as shown in FIG. 1H, pretreatment with doxorubicin overcame the cells' resistance to PS-341 and the combination of doxorubicin and PS-341 resulted in significant MM cell death. Thus, synergy between PS-341 and chemotherapy can reverse resistance to either agent alone.

Example 9

PS-341 Abolishes Cell Adhesion-Mediated Drug Resistance (CAM-DR)

Whether PS-341 abolishes cell adhesion-mediated drug resistance (CAM-DR) was studied. MM.1S cells were treated for 24 h with doxorubicin (100-200 ng/ml) in wells coated with or without fibronectin (FN). PS-341 (10 nM) was added for additional 24 h. In all cases, % cell survival (mean±SD) is quantified by MU. All experiments were repeated at least three times, and each experimental condition was repeated at least in quadruplicate wells in each experiment.

Figure 1I:
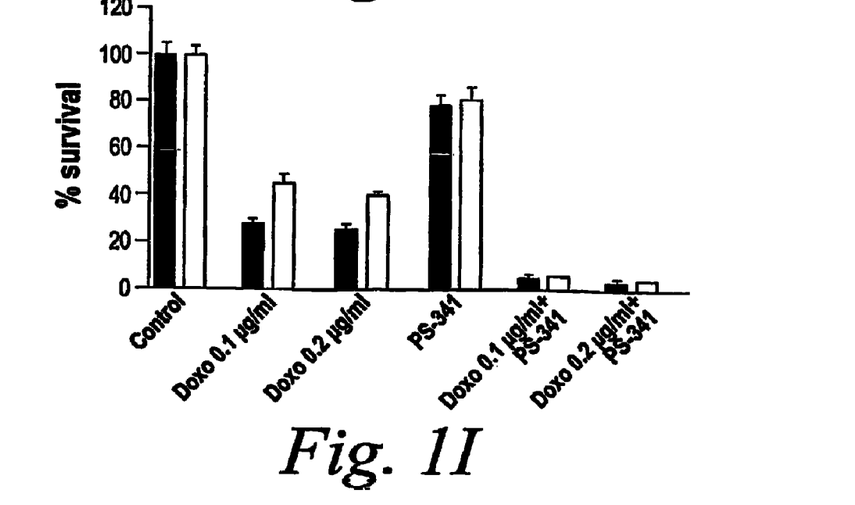
FIG. 1I illustrates a study where MM.1S cells were treated for 24 h with doxorubicin (100-200 ng/ml) in wells coated with (white bars) or without (black bars) fibronectin (FN). PS-341 (10 nM) was added for additional 24 h. In all cases, % cell survival (mean±SD) is quantified by MTT.

The sensitivity of MM cells to doxorubicin is decreased upon tumor cell binding to extracellular matrix components, in particular fibronectin. This cell adhesion-mediated drug resistance (CAM-DR) is associated with increased availability of the caspase inhibitor, FLIP, for binding to the death receptor Fas and decreased activation of caspase-8. PS-341 lowers FLIP expression and facilitates Fas-dependent caspase-8 activation. As shown in FIG. 1I, MM.1S cells are less sensitive to doxorubicin in the presence than in the absence of fibronectin, but PS-341 completely overcomes this anti-apoptotic effect (P<0.05). Thus, PS-341 abolishes cell adhesion-mediated drug resistance (CAM-DR).

Example 10

The Mechanism of Chemosensitization by PS-341

Figure 2A:
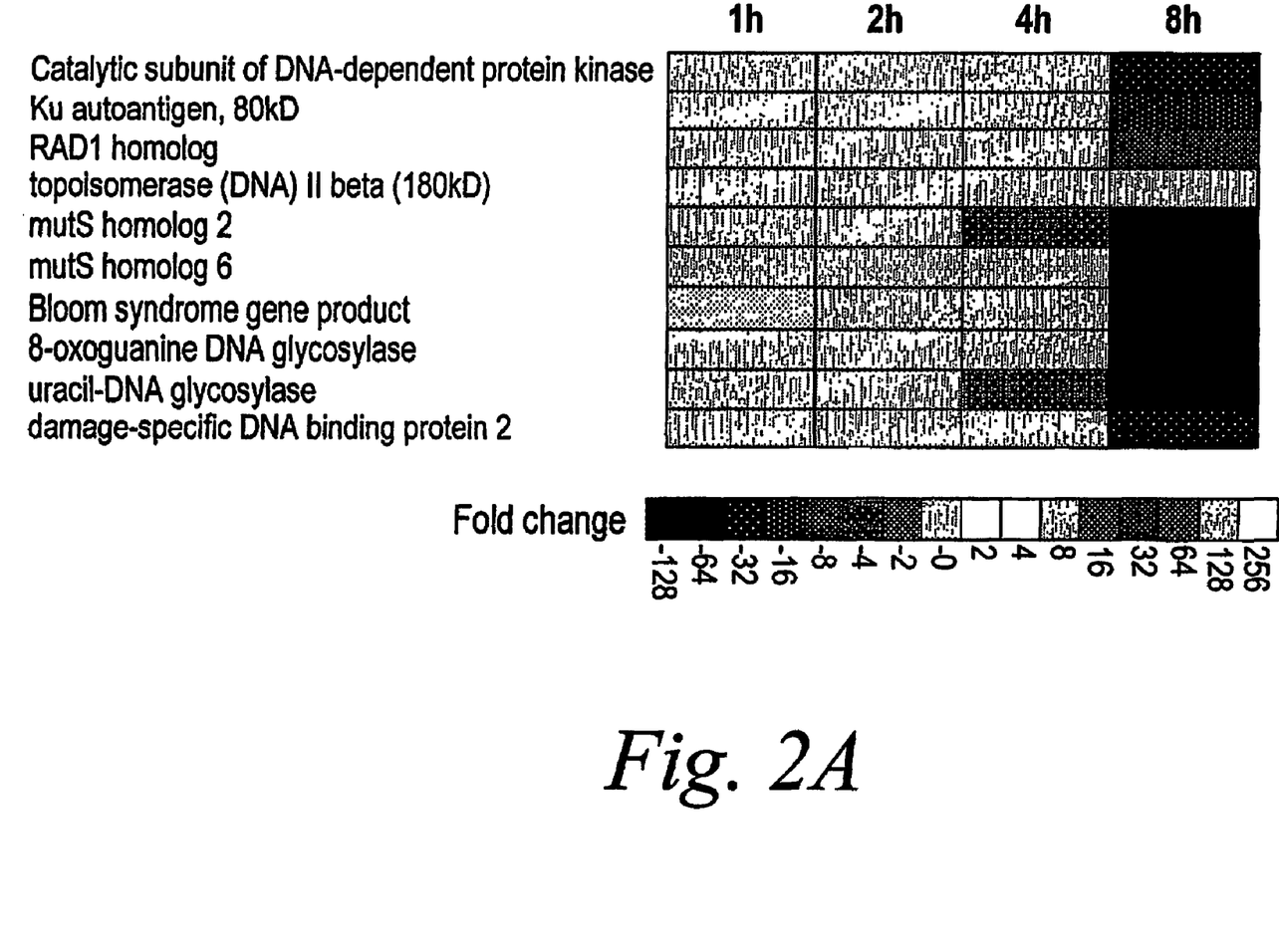
FIG. 2A illustrates a transcriptional profile detected by oligonucleotide-microarray analysis in MM-1S cells treated with PS-341. Transcriptional changes induced by PS-341 (100 nM, 1-8 h) included downregulation of a functional cluster of molecules implicated in the response to genotoxic stress. Color saturation is proportional to magnitude of the difference from the respective control.

PS-341 decreases the expression of Bcl-2, A1, cIAP-2, XIAP and FLIP. These effects may be due, at least in part, to the inhibition of NF-kB activation by PS-341, since specific inhibition of NF-kB down-regulates these apoptosis inhibitors and sensitizes MM cells to doxorubicin. To further study the mechanism of chemosensitization by PS-341, transcriptional profiles of MM-1S cells treated with PS-341 versus control cells were detected using oligonucleotide-microarray analysis (FIG. 2A). PS-341 induces changes in transcripts involved in the regulation of apoptosis, cell growth, proteasome function, and heat shock response. The effect of PS-341 on transcripts in response to chemotherapy were specifically studied. The results showed that transcriptional changes induced by PS-341 (100 nM, 1-8 h) include down-regulation of a functional cluster of molecules implicated in the response to genotoxic stress. Specifically, PS-341 down-regulated the transcripts for several effectors of the protective cellular response to genotoxic stress: topoisomerase II beta, that relaxes DNA torsion upon replication, transcription, and cell division and is inhibited by mitoxantrone, doxorubicin, and etoposide (Hazlehurst, L. A., et al. *Blood* 98:1897, 2001); the Bloom syndrome gene product, involved in maintenance of genome integrity and stability through its cooperation with p5320; 8-oxoguanine DNA glycosylase and uracil-DNA glycosylase, involved in base-excision repair and protection from oxidative DNA damage (Rosenquist, T A, et al. *Proc Natl Acad Sci, USA* 94:7429, 1997); the mutS homologs 2 and 6, that are involved in mismatch repair (Sixma, T. K. *Curr Opin Struct Biol* 11:47, 2001); the catalytic subunit of DNA-dependent protein kinase and Ku autoantigen, which function in the repair of DNA double-strand breaks caused by physiological oxidation reactions, V(D)J recombination, ionizing radiation, and chemotherapeutic drugs (Featherstone, C. and Jackson, S. P. *Curr Biol* 9:R759, 1999); the damage-specific DNA binding protein 2; and the RAD1 homolog, which is involved in nucleotide excision repair and recombination repair.

Figure 2B:
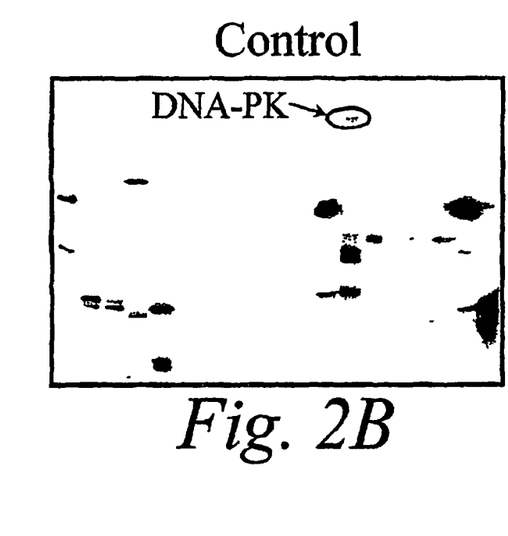
FIGS. 2B-2C illustrate a proteomic analysis of the signaling state of PS-341-treated MM-1S cells which detects proteomic analysis down-regulation of DNAPK following 8-hour incubation with PS-341 (as depicted by respective arrows).
Figure 2C:
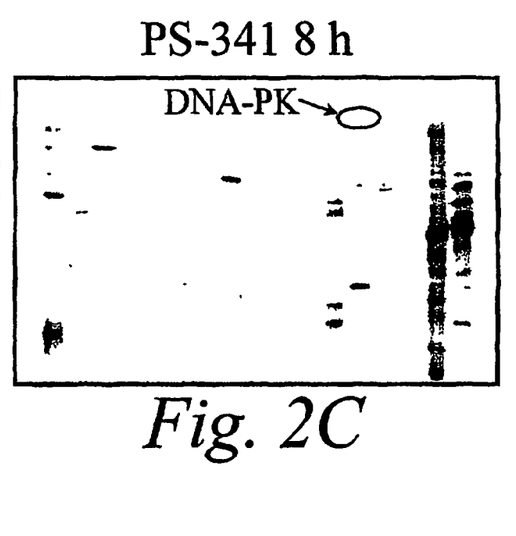
Figure 2D:
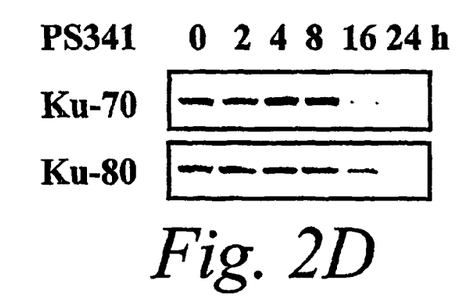
FIG. 2D illustrates an immunoblot confirming that PS-341 decreases protein expression of Ku80 and Ku70.

Selected changes were further confirmed at the protein level. Proteomic analysis of the signaling state of PS-341-treated MM-1S cells which detects proteomic analysis confirmed the down-regulation of DNA-dependant protein kinase following 8-hour incubation with PS-341 (FIGS. 2B-2C). Moreover, conventional immunoblotting confirmed the time-dependent down-regulation of the Ku subunits (80 and 70 kD) triggered by PS-341 (FIG. 2D).

In a Phase II multi-center clinical trial of PS-341 treatment of patients with relapsed, refractory MM, remarkable antitumor activity has been demonstrated, including some complete responses. Significant sensitization to anticancer therapies by proteasome inhibitors without increased toxicity, has also been demonstrated in other animal models, independent of functional p53 status.

We claim:

1. A method for treating multiple myeloma in a subject wherein the subject's cancer cells are resistant to treatment with the proteasome inhibitor PS-341, comprising administering to the subject an effective amount of PS-341 and an effective amount of doxorubicin such that multiple myeloma is treated.

2. The method of claim 1, wherein the treatment of multiple myeloma is due to the inhibition of tumor growth.

3. The method of claim 1, further comprising the administration of at least one additional proteasome inhibitor or chemotherapeutic agent.

4. The method of claim 1, wherein PS-341 is administered prior to the administration of doxorubicin.

5. The method of claim 1, wherein PS-341 is administered simultaneously with the administration of doxorubicin.

6. The method of claim 1, wherein PS-341 is administered after the administration of doxorubicin.

7. The method of claim 1, wherein PS-341 and doxorubicin are administered intravenously.

8. The method of claim 1, wherein PS-341 and doxorubicin are administered intraperitoneally.

9. The method of claim 1, wherein PS-341 and doxorubicin are administered orally.

10. A method for treating multiple myeloma in a subject, wherein the subject's cancer cells are resistant to treatment with the proteasome inhibitor PS-341, comprising administering to the subject an effective amount of PS-341 and an effective amount of doxorubicin such that multiple myeloma is treated, wherein PS-341 is administered at a dose of about 0.001 mg/m$^2$ body surface area/day to about 4.0 mg/m$^2$ body surface area/day.

11. The method of claim 10, wherein the treatment of multiple myeloma is due to the inhibition of tumor growth.

12. The method of claim 10, further comprising the administration of at least one additional proteasome inhibitor or chemotherapeutic agent.

13. The method of claim 10, wherein PS-341 is administered prior to the administration of doxorubicin.

14. The method of claim 10, wherein PS-341 is administered simultaneously with the administration of doxorubicin.

15. The method of claim 10, wherein PS-341 is administered after the administration of doxorubicin.

16. The method of claim 10, wherein PS-341 and doxorubicin are administered intravenously.

17. The method of claim 10, wherein PS-341 and doxorubicin are administered intraperitoneally.

18. The method of claim 10, wherein PS-341 and doxorubicin are administered orally.

* * * * *